United States Patent
Coyle et al.

(10) Patent No.: US 10,398,469 B2
(45) Date of Patent: Sep. 3, 2019

(54) EXPANDABLE INTRODUCER SHEATH

(71) Applicant: Creganna Unlimited Company, Galway (IE)

(72) Inventors: James Coyle, Galway (IE); Bernard McDermott, Mayo (IE); Brendan Marrinan, Galway (IE); Liam Farrissey, Galway (IE); Adam Szczepanski, Galway (IE)

(73) Assignee: Creganna Unlimited Company, Galway (IE)

( * ) Notice: Subject to any disclaimer, the term of this patent is extended or adjusted under 35 U.S.C. 154(b) by 106 days.

(21) Appl. No.: 15/211,086

(22) Filed: Jul. 15, 2016

(65) Prior Publication Data

US 2017/0014157 A1    Jan. 19, 2017

Related U.S. Application Data

(60) Provisional application No. 62/193,979, filed on Jul. 17, 2015.

(51) Int. Cl.

| | |
|---|---|
| *A61B 17/34* | (2006.01) |
| *A61M 25/00* | (2006.01) |
| A61B 17/00 | (2006.01) |
| A61M 25/06 | (2006.01) |

(52) U.S. Cl.
CPC ...... *A61B 17/3439* (2013.01); *A61B 17/3415* (2013.01); *A61B 17/3423* (2013.01); *A61B 17/3431* (2013.01); *A61B 17/3498* (2013.01); *A61M 25/0023* (2013.01); *A61B 2017/00871* (2013.01); *A61B 2017/3441* (2013.01); *A61M 25/0662* (2013.01); *A61M 2025/0024* (2013.01)

(58) Field of Classification Search
CPC ............ A61B 17/3415; A61B 17/3423; A61B 17/3431; A61B 17/3439; A61B 17/3498; A61B 2017/00871; A61B 2017/3441; A61M 2025/0024; A61M 25/0023; A61M 25/0662

See application file for complete search history.

(56) References Cited

U.S. PATENT DOCUMENTS

| | | | |
|---|---|---|---|
| 5,882,345 A | 3/1999 | Yoon | |
| 2009/0319019 A1 | 12/2009 | Parker | |
| 2012/0083877 A1 | 4/2012 | Nguyen et al. | |
| 2017/0151080 A1* | 6/2017 | Williams | ............... A61F 5/0036 |

FOREIGN PATENT DOCUMENTS

| | | |
|---|---|---|
| WO | 2004/037333 A1 | 5/2004 |
| WO | 2006/029370 A2 | 3/2006 |
| WO | 2009/097650 A1 | 8/2009 |

\* cited by examiner

*Primary Examiner* — Imani N Hayman
(74) *Attorney, Agent, or Firm* — Schiff Hardin LLP

(57) ABSTRACT

An expandable introducer sheath for use in interventional procedures. The expandable introducer sheath can be inserted into a treatment vessel in a first unexpanded configuration. The expandable introducer sheath can expand in diameter during insertion of a device through its main lumen and can then re-collapse down to its unexpanded diameter. The device comprises an inner heat-set folded layer and an outer elastomeric layer. The outer elastomeric layer provides a barrier between the inner folded layer and a vessel wall during unfolding of the inner folded layer to minimize the risk of vessel trauma.

12 Claims, 7 Drawing Sheets

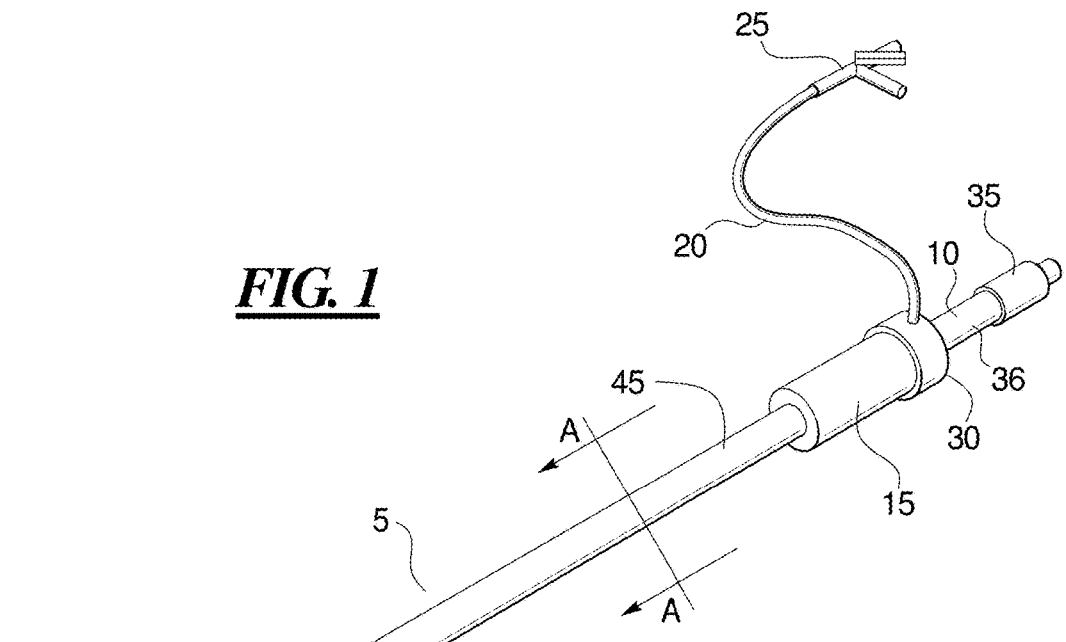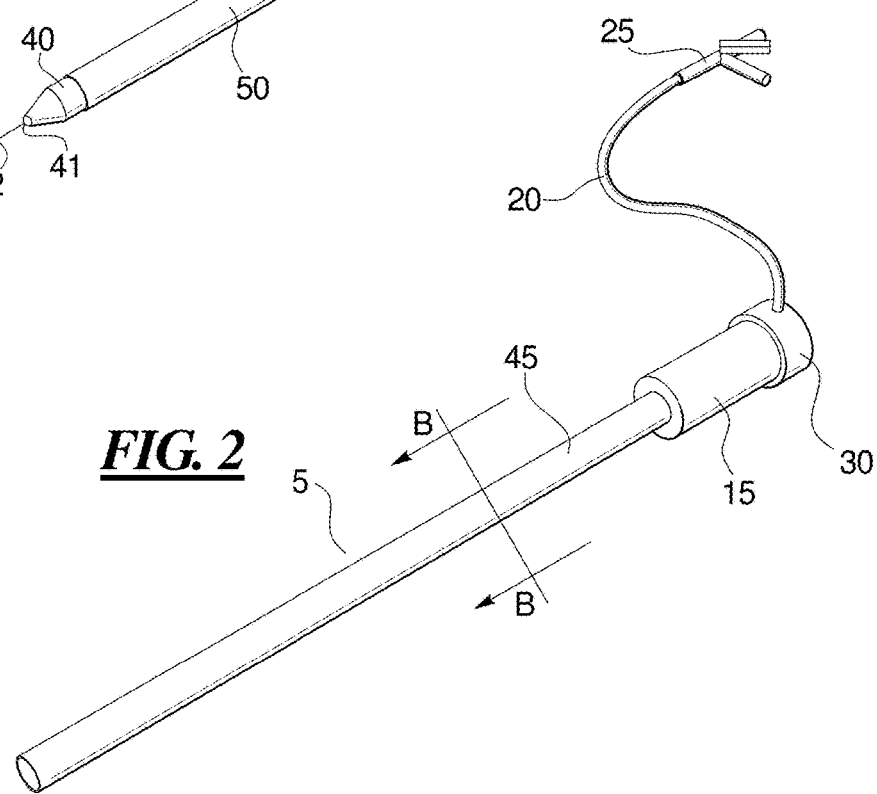

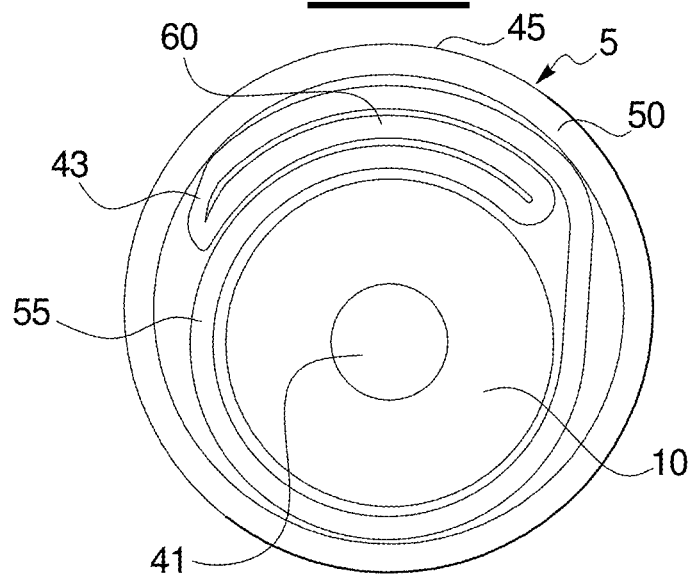
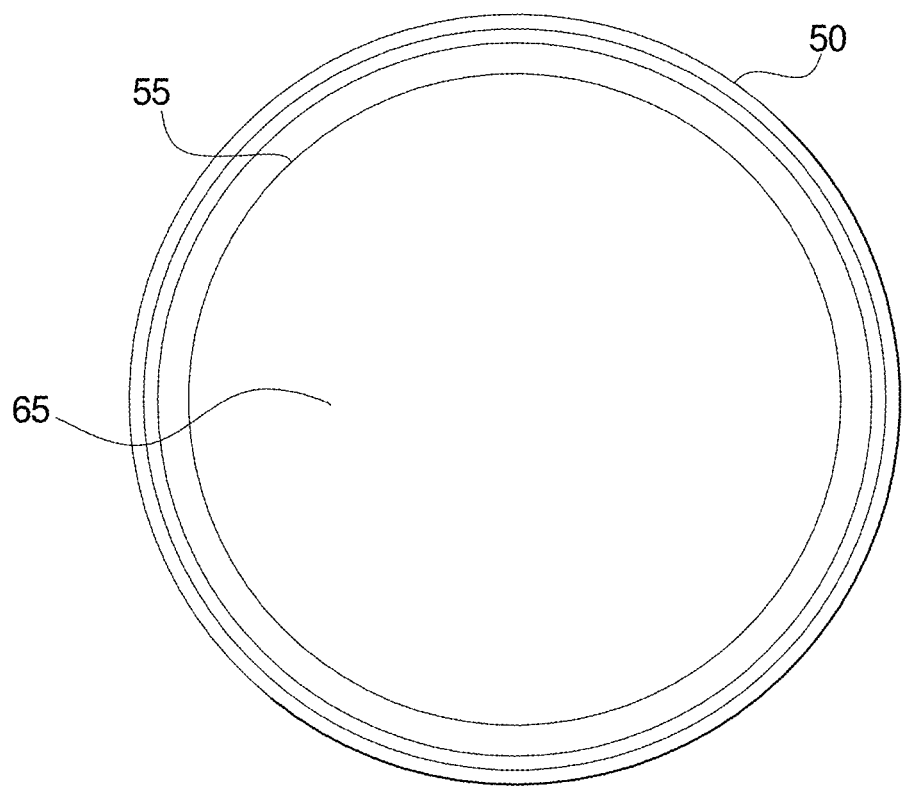

EXPANDABLE INTRODUCER SHEATH

CROSS REFERENCE TO RELATED APPLICATION

The present application claims the benefit of U.S. Provisional Patent Application Ser. No. 62/193,979, filed on Jul. 17, 2015, which application is incorporated herein by reference.

BACKGROUND OF THE INVENTION

Field of the Invention

The present invention relates generally to an introducer for expanding an opening into the body for a medical procedure.

Description of the Related Art

Introducer sheaths are used in a variety of interventional procedures for access into a patient's artery for the purposes of providing a lumen for the passage of other interventional devices such as balloon catheters, stents, guide catheters, temporary heart pumps, artificial heart valves and guide wires. Introducer sheaths typically comprise a tubular element with a hub at the proximal end (the end proximal to the doctor or other medical professional) and a dilator inserted within the tubular element. The hub typically has a valve at the proximal end to prevent blood loss through the lumen during insertion of devices through the valve and the main lumen of the introducer. The hub also incorporates a port and a tube terminating in a stop cock. A syringe containing saline (for example) may be connected to the stopcock to flush any air out of the annular space between the dilator and the introducer shaft prior to insertion of the introducer within a patient's vessel. A Luer connector at the proximal end of the dilator may also be used for flushing air out of the inner lumen of the dilator prior to using the introducer. The dilator can be inserted into the lumen of the introducer prior to insertion into a patient's vessel. The dilator is tapered at the distal end (the end distal to the doctor or other medical professional) and has a central lumen for tracking over a guide wire. The dilator serves to provide a transition between the guide wire and the introducer internal diameter during advancement of the introducer into a patient's vessel.

Introducers come in a variety of different sizes depending on the procedure being performed. For example, a coronary stenting procedure may utilize a size 5 F or 6 F introducer sheath. The sizes 5 F or 6 F refer to French catheter sizes (also referred to as Fr sizes), wherein a round catheter of size 1 French (1 F or 1 Fr) has an external diameter of ⅓ mm. A size 6 F catheter has an external diameter of 2 mm. The introducer sheath/dilator may be inserted into a patient vessel over a pre-positioned 0.035" (0.035 inch) guide wire. The dilator resides within the inner lumen of the introducer during access into the patient's vessel. After the introducer is in position, the guide wire and the dilator may be removed, leaving the introducer in situ. A valve at the proximal end of the introducer prevents blood loss from the patient through the introducer while also allowing devices to be inserted through this valve. During a coronary angioplasty procedure, for example, a size 5 F or 6 F guide catheter may be advanced through the main lumen of the introducer and advanced through the patient's vasculature. The tip of the guide catheter may be positioned in the ostium of the vessel being treated. Balloons and stent delivery systems may then be advanced through the guide catheter lumen.

In more recent years, larger diameter introducers are being used for specific procedures that require a delivery system with a large profile. During aortic valve replacement, for example, the delivery system profile may be as large as size 18 F-22 F. This larger delivery system profile requires an introducer sheath with an inner diameter of size 19 F-24 F, for example. In such instances the introducer outer diameter may be size 24 F (8 mm). These introducers are typically inserted into the femoral artery. For some patients their femoral artery may be less than 8 mm diameter so that it would not be possible to treat certain patients with specific delivery systems that have a profile or outside diameter that is too large for the blood vessels of the particular patient. To address this shortcoming, some companies have developed expandable-type introducer sheaths that have a specific profile during delivery into the patient's vasculature and are capable of a certain amount of expansion during advancement of the large profile delivery system through the introducer inner lumen. These commercially available introducers have several drawbacks.

One commercially available expandable introducer comprises a sheath with a longitudinal slit along its length. The sheath is then folded inside itself so that its profile, or external diameter, is significantly lower, or less, than the original profile. A very thin layer of material connects both sides of the longitudinal slit. Upon advancing of the delivery system through this introducer the sheath unfolds but when it does so it leaves an edge protruding along the length of the sheath. The edge presents a risk of vessel trauma or injury during the remainder of the procedure and when the introducer is being removed from the patient. In addition the forces required to advance the delivery system through this introducer can be as high as 25 Newton's. This represents a potential risk for patient injury.

Another commercially available introducer comprises a braided-type shaft that is folded down into a reduced profile configuration and a balloon catheter residing within the internal lumen of the introducer. When the introducer is advanced in position the balloon can be inflated to expand the introducer profile within the vessel. The balloon catheter can then be removed and the delivery system can then be passed through the introducer. The introducer profile does not revert to its original lower profile after the delivery system has been passed through the introducer so that this introducer only provides for a lower profile (smaller external diameter) initially during insertion into the patient vessel. In addition, the balloon catheter within the introducer requires additional steps that must be completed when using this introducer such as purging the balloon catheter, inflating the balloon catheter and removal of the balloon catheter. The balloon catheter must remain inflated for one minute during expansion of the introducer. This is a time related disadvantage with this introducer.

It is therefore desirable to have an expandable introducer sheath that is capable of atraumatic expansion and that provides for lower insertion forces for devices being inserted through the expandable introducer sheath.

SUMMARY OF THE INVENTION

Certain embodiments of the present invention provide an introducer sheath having a first unexpanded profile and being configured for insertion into a patient's vasculature. The introducer may be capable of sufficient atraumatic expansion such that the introducer permits advancing of large profile devices through its lumen. The introducer may then collapse down to its original profile after the large profile device has passed through the lumen. The introducer may comprise an inner shape-memory folded layer and an outer elastomeric layer that provides a cover over the inner folded layer. The outer elastomeric layer may cover the folded layer when the folded layer is unfolding during expansion to minimize the risk of vessel trauma. The outer elastomeric layer may cover the folded layer during refolding of the folded layer to further minimize vessel trauma. The outer elastic layer may also serve to rewrap the inner folded layer after expansion and may aid in refolding of the inner folded layer.

BRIEF DESCRIPTION OF THE DRAWINGS

FIG. 1 is a perspective view of expandable introducer sheath in an unexpanded configuration in accordance with one embodiment of the invention.

FIG. 2 is the same perspective view of the embodiment shown in FIG. 1 in an expanded configuration.

FIG. 3 is a cross sectional view of the embodiment shown in FIG. 1.

FIG. 4 is a cross sectional view of the embodiment shown in FIG. 2.

DETAILED DESCRIPTION OF THE PREFERRED EMBODIMENTS

Figure 5:
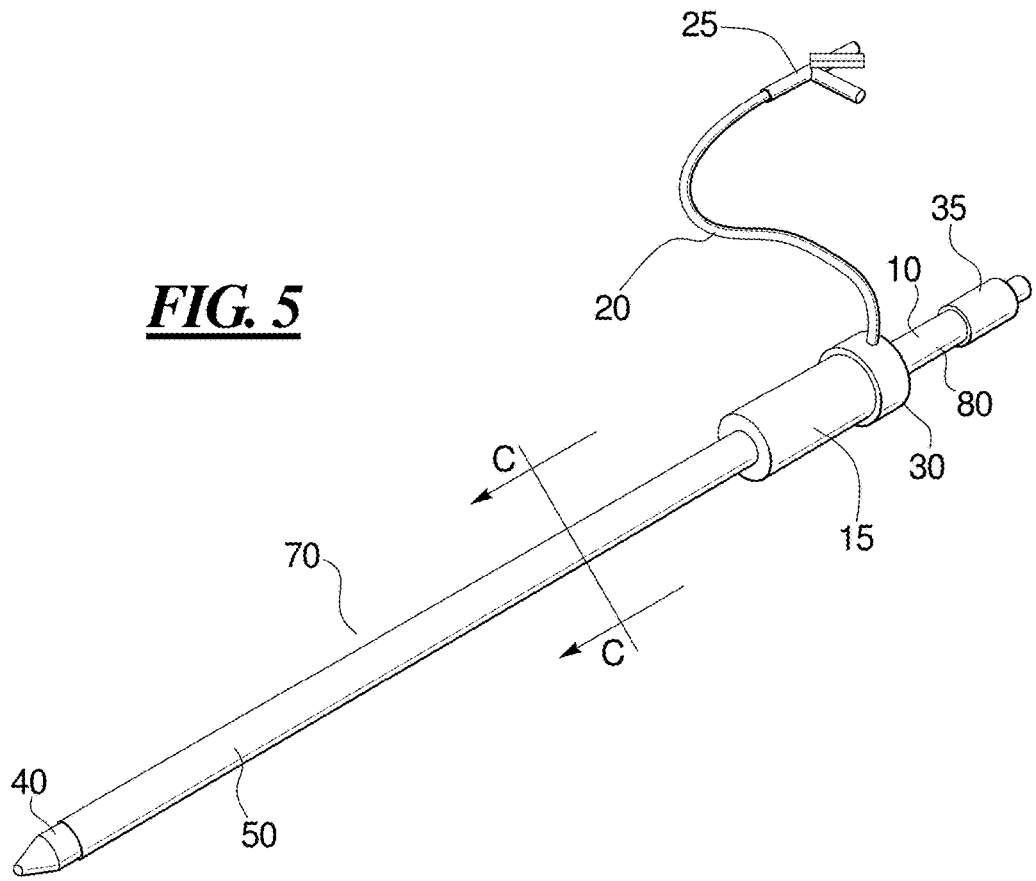
FIG. 5 is a perspective view of an expandable introducer sheath in accordance with another embodiment of the invention.

Specific embodiments of the present invention are now described with reference to the figures, wherein like reference numerals indicate identical or functionally similar elements. The following detailed description is merely exemplary in nature and is not intended to limit the invention or the application and uses of the invention.

FIG. 1 shows a perspective view of an expandable introducer sheath 5 in an unexpanded configuration in accordance with one embodiment of the invention. FIG. 2 shows a perspective view of the embodiment shown in FIG. 1 in an expanded configuration with the dilator omitted from this drawing. The expandable introducer sheath 5 comprises a hub 15 attached to shafts 45. The hub 15 serves as a gripping member during advancement of the expandable introducer sheath 5 into a patient's vasculature. A sealing valve 30 at the proximal end of the hub 15 ensures there is no or little blood loss through the sheath during advancement of devices through the main lumen of the expandable introducer sheath 5. The hub 15 is in communication with a tube 20 that is attached to a stop cock 25. A syringe (not shown) containing saline solution can be connected to the stop cock 25 for the purpose of flushing the expandable introducer sheath 5 prior to use via a tube 20. A dilator 10 resides within the main lumen of the expandable introducer sheath 5. A Luer connector 35 at a proximal end 36 of the dilator 10 allows for flushing of the central lumen of the dilator 10 prior to use. A distal end 40 of the dilator 10 protrudes distally past the end of the shafts 45 of the expandable introducer sheath 5. The dilator distal end 40 ensures that there is a transition in profile from the distal end of the dilator distal end 40 up to the distal end of the shafts 45 of the expandable introducer sheath 5. A central lumen 41 runs through the dilator 10 for accommodating guide wires, such as a guide wire 42. The expandable introducer sheath 5 includes an outer layer 50.

FIG. 3 shows a sectional view in the direction of the arrows A-A in FIG. 1. The shafts 45 of the expandable introducer sheath 5 are comprised of an inner folded layer 55 and outer elastomeric layer 50. The inner folded layer 55 is folded down to a reduced diameter by means of folds 60 formed in the inner folded layer 55. The folds 60 may be formed into the material of the inner folded layer by a mechanical process and may be heat set or otherwise shape-memory set in position so that the inner folded layer 55 retains its folded shape until expanded and returns to its folded shaped even after expansion. The outer elastomeric layer 50 encapsulates the inner folded layer 55 and acts as a barrier between the inner folded layer 55 and a vessel wall during expansion of the inner folded layer 55. The outer elastomeric layer 50 may be coated on its outer surface to reduce friction and to enable easier advancement of the expandable introducer sheath 5 during use. The outer elastomeric layer 50 also serves to assist with the refolding or folding down of the inner folded layer 55 after expansion of the inner folded layer 55 has occurred as a result of passage of devices through the main lumen of the expandable introducer sheath 5. In other words, portions of the inner folded layer 55 expand and unfold during passage of a large diameter device as the device passes through the inner lumen of the inner folded layer 55. After the device has passed through a portion of the expandable introducer sheath 5, the shape memory of the inner folded layer 55 causes the inner folded layer to return to a folded, non-expanded shape. The outer elastomeric layer 50 exerts compressive forces on the inner folded layer, urging the inner folded layer 55 back to the folded and non-expanded condition according to the shape memory of the layer 55. The sheath 5 is returned to its original diameter or at least returned to nearly its original diameter after the large diameter device has passed through the sheath 5. In certain embodiments the sheath 5 returns to a diameter that is greater than its diameter prior to expansion. In certain embodiments the sheath 5 returns to a diameter less than the diameter to which the sheath 5 was expanded by the passage of the device through the sheath 5.

As can be seen in FIG. 3 the dilator 10 resides within the central lumen of the expandable introducer 5 and the dilator 10 has a central lumen 41 to accommodate a guide wire during insertion of the expandable introducer sheath 5 into a patient's vasculature. In the embodiment shown in FIG. 3, the inner folded layer 55 incorporates folds 60 at one location about its circumference but additional embodiments could incorporate two or more folds similar to the folds 60 about the circumference of the inner folded layer 55.

FIG. 4 shows a sectional view in the direction of the arrows B-B in FIG. 2. The inner folded layer 55 and the outer elastomeric layer 50 are shown expanded in FIG. 4. During insertion of devices, for example devices having a large diameter, through a central lumen 65 of the expandable introducer sheath 5 the inner folded layer 55 can unfold to a larger internal diameter. When a device is being passed through central lumen 65 of the expandable introducer sheath 5 the device may contact and expand inner folded layer 55 and consequently expand the outer elastomeric layer 50. After passage of the device through the central lumen 65 of expandable introducer sheath 5, the inner folded layer 55 may refold down to the configuration shown in FIG. 3 or to a similar configuration. The outer elastomeric layer 50 may provide additional collapsing force on the inner folded layer 55 after passage of a device through the central lumen 65 of the expandable introducer sheath 5. A portion 43 of the fold 60 is shaped to facilitate refolding with the aid of the outer elastomeric layer 50, for example, by thinning the portion 43 at the edge of the fold.

The inner folded layer 55 may be extruded from a suitable polymer material such as Grilamid, Vestamid, HDPE, LDPE or pebax that can be shape-set into a formed shape using heat or other means so that the folds 60 of the inner folded layer 55 retain their shape and return to their folded shape even after unfolding of the inner folded layer 55. The inner folded layer 55 may also be formed from any material or process that results in a material that can be folded down into a lower profile, or smaller diameter. The inner folded layer 105 in FIGS. 7 and 8 may be subjected to further processing to enable ease of folding and unfolding of the inner folded layer 105. Polymer laser ablation may be employed to reduce the thickness of the wall of inner folded layer 105 along the fold of inner folded layer 105 so that the inner folded layer 55 can be more easily folded into the configuration shown in FIG. 3 and the inner folded layer 55 will be more easily expandable. Other processes may also be employed to reduce the wall thickness of the inner folded layer 105 along a fold line 110 of the inner folded layer or otherwise shape the inner folded layer or outer elastomeric layer.

The outer elastomeric layer 50 may be formed from an elastic material that is capable of sufficient expansion as to permit full expansion of the inner folded layer 55. The elastic material may have sufficient elastic strength that it is able to aid compression of the inner folded layer to its folded shape. The outer elastomeric layer may be formed from pellethane, tecothane, tecoflex, quadrathane, desmopan, polyblend, chronoprene or any other elastomeric material capable of sufficient radial expansion to permit passage of the device within the lumen of the sheath 5. Alternately, the outer elastomeric layer 50 may be formed from a non-elastic material that encapsulates the inner folded layer 55. The outer elastomeric layer 50 may be formed by extrusion, dip coating or any other process that results in a tubular elastomeric or non-elastomeric material.

Figure 6:
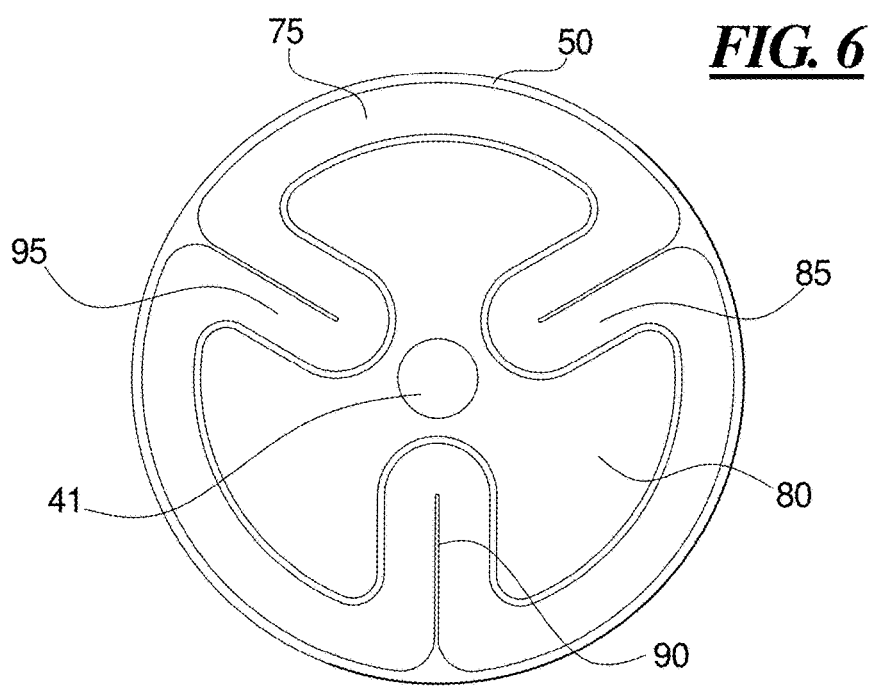
FIG. 6 is a cross sectional view of the embodiment shown in FIG. 5

FIG. 5 shows a perspective view of an expandable introducer sheath 70 in accordance with another embodiment of this invention. FIG. 6 shows a cross sectional view in the direction of arrows C-C in FIG. 5. The inner folded layer 75 comprise three separate folds 85, 90 and 95 that project inwards from the outer surface of the inner folded layer 75. A dilator 80 has three separate indentations that accommodate the three separate folds 85, 90 and 95 of the inner folded layer 75. The dilator 80 serves to lock the inner folded layer 75 in an unexpanded configuration so that the inner folded layer 75 may not expand in diameter until the dilator 80 is removed. Three separate folds 85, 90 and 95 serve to ensure that the inner folded layer 75 may expand concentrically during passage of devices through the central lumen of the expandable introducer sheath 70. The outer elastomeric layer 50 serves to provide a barrier between the inner folded layer 75 and a vessel wall during expansion of and unfolding of the inner folded layer 75. The outer elastomeric layer 50 also serves to assist the inner folded layer 75 to re-collapse down or re-fold after expansion following passage of devices through the main lumen of the expandable introducer sheath 70.

Figure 7:
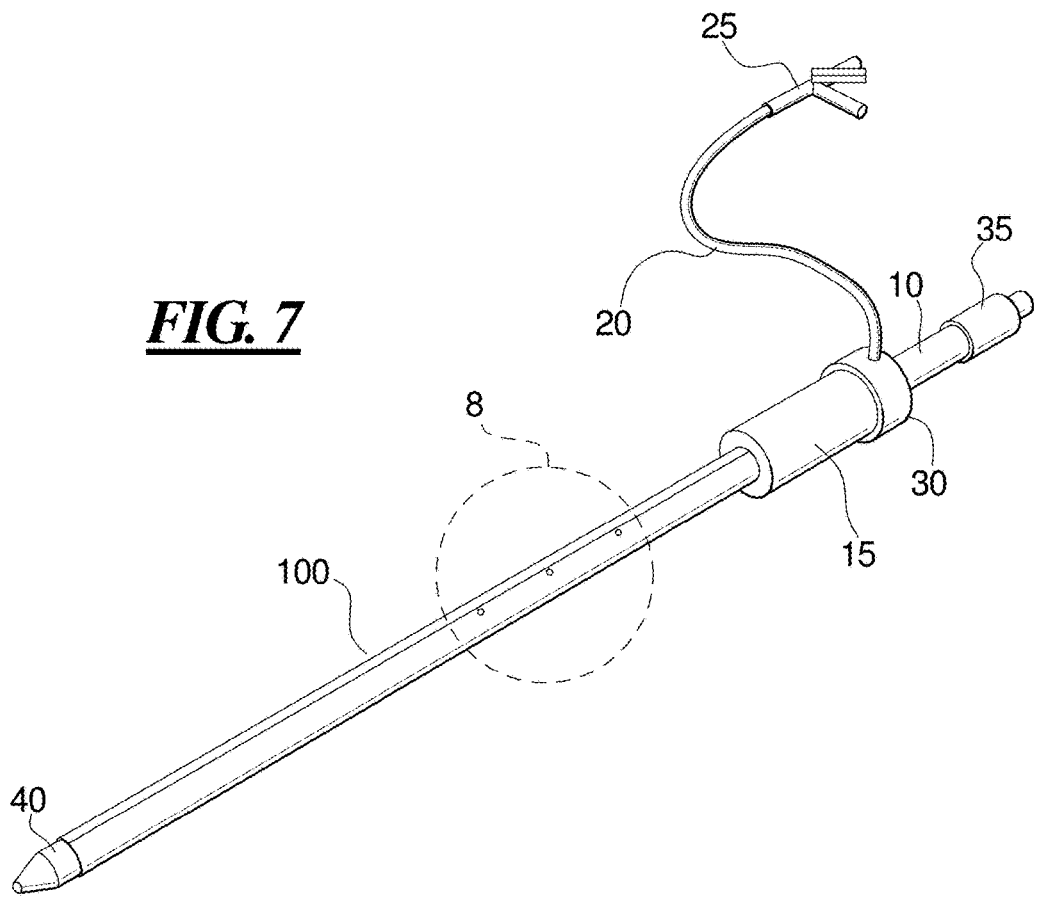
FIG. 7 is a perspective view of an expandable introducer sheath in accordance with another embodiment of the invention.
Figure 8:
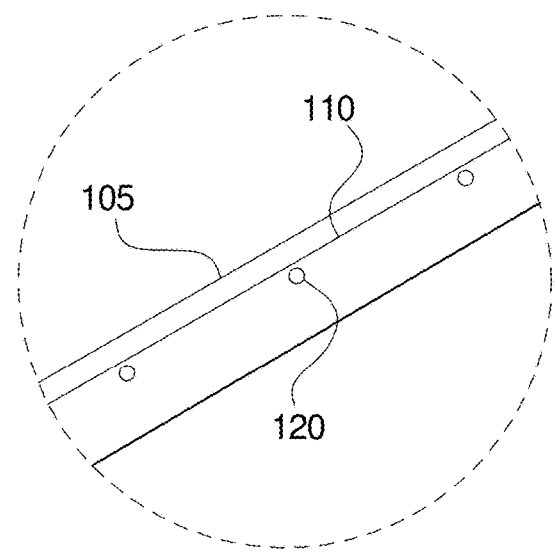
FIG. 8 is an enlarged view of the area circled and labelled 8 in FIG. 7

FIG. 7 shows an expandable introducer sheath 100 in accordance with another embodiment of this invention with the outer elastomeric layer 50 omitted to clearly show the inner folded layer it would otherwise obscure. FIG. 8 is an enlarged view of the area circled and labelled 8 in FIG. 7. The inner folded layer 105 incorporates a single fold 110. Punch holes or openings 120 adjacent to the fold 110 of the inner folded layer 105 provide holes through the wall of the inner folded layer 105. During purging of the expandable introducer sheath 100 a syringe containing saline solution may be attached to the stop cock 25 and fluid may be injected into the annular space between the inner folded layer 105 and the dilator 10. Fluid may pass through the punch holes 120 from inside the inner folded layer 105 to the space between the inner folded layer 105 and the outer elastomeric layer 50 to enable the removal of any air between the inner folded layer 105 and the elastomeric outer layer 50.

Figure 9:
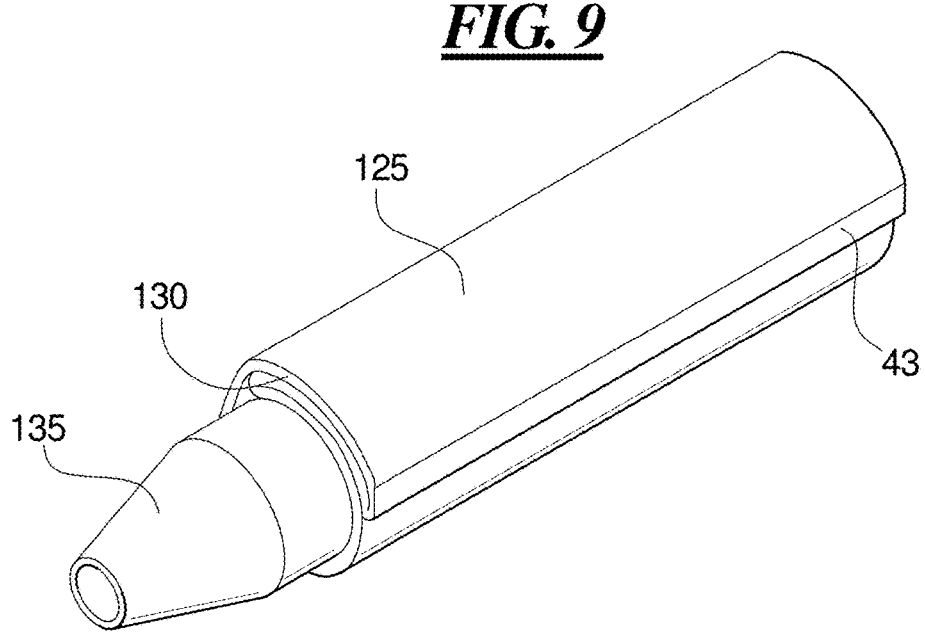
FIG. 9 is a perspective view of the distal end of the dilator and inner folded layer of an expandable introducer sheath in accordance with another embodiment of this invention.

FIG. 9 shows distal end of an inner folded layer 125, a dilator distal end 135 and distal edge 130 of an inner folded layer 125. The distal edge 130 of the inner folded layer 125 consists of three layers of material in the region of the folded portion.

The three layers are apparent at the distal end of the inner folded layer 125. The three layers in the folded region cause an abrupt increase in profile (diameter) from dilator distal end 135 to the distal end of the inner folded layer 125 because the folded portion of distal end of inner folded layer 125 is three times thicker than the wall of distal end of inner folded layer 125. A shaped part 43 of the fold is visible in the figure.

Figure 10:
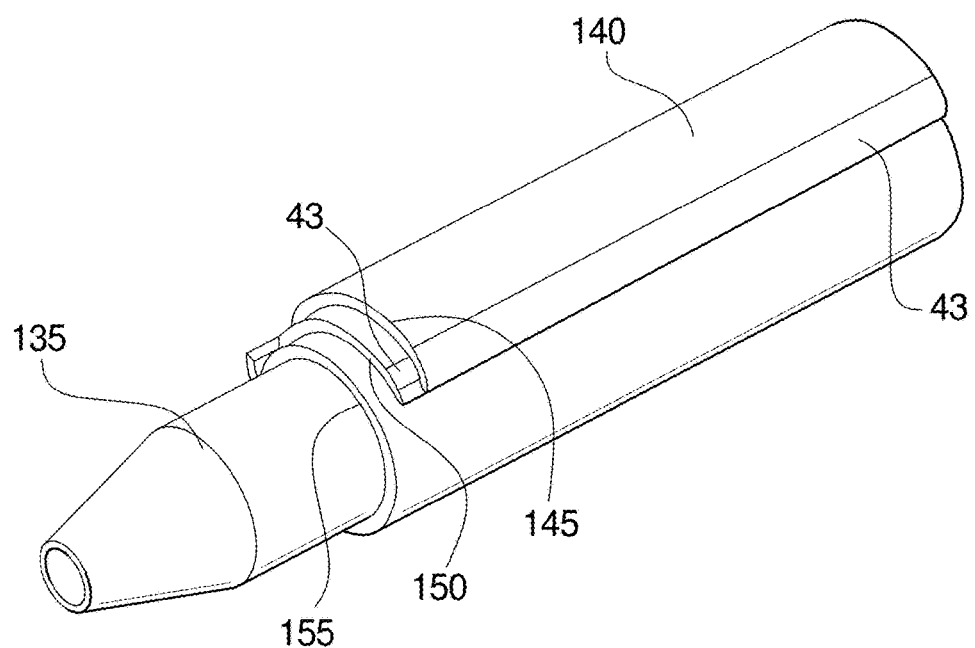
FIG. 10 is a perspective view of the distal end of the dilator and inner folded layer of an expandable introducer sheath in accordance with another embodiment of this invention.

FIG. 10 shows distal end of inner folded layer 140 in accordance with another embodiment of the invention. A distal edge 155 of the inner folded layer 155 resides upon the dilator distal end 135. A recessed segment 150 of the distal edge of the inner folded layer is recessed from the distal edge of the inner folded layer 155 so that the increase in profile from the dilator distal end 140 to the distal edge 155 of the inner folded layer is equivalent to the wall thickness of the shaft.

A recessed segment 145 of the distal edge of the inner folded layer is in turn recessed from the segment 150 of the distal edge of the inner folded layer so that the maximum increase in profile from the dilator distal end 140 is more gradual than if the folded edges were not recessed. In addition, the recessed segment 145 of the distal edge of inner folded layer, the recessed segment 150 of the distal edge of the inner folded layer and the distal edge 155 of the inner folded layer can also be tapered at the distal edge to further transition the increase in profile from the dilator distal end 140 to the distal end of the inner folded layer 135.

Figure 11:
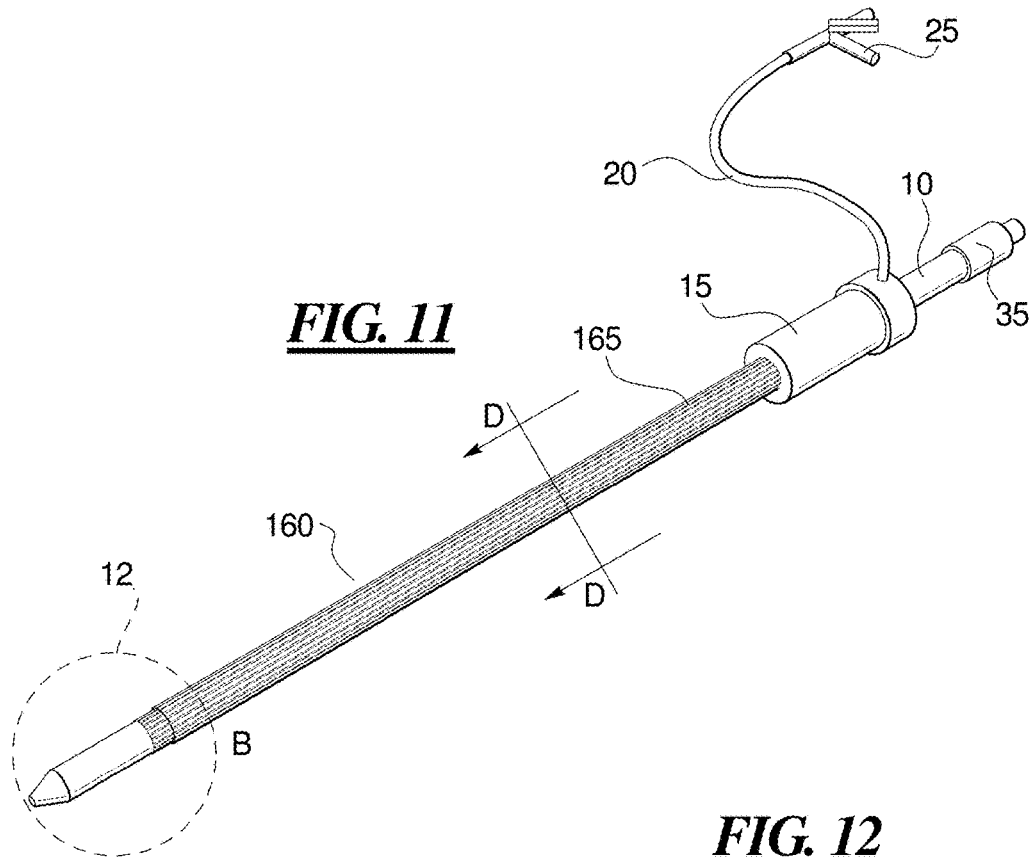
FIG. 11 is a perspective view of an expandable introducer sheath in accordance with another embodiment of the invention.
Figure 12:
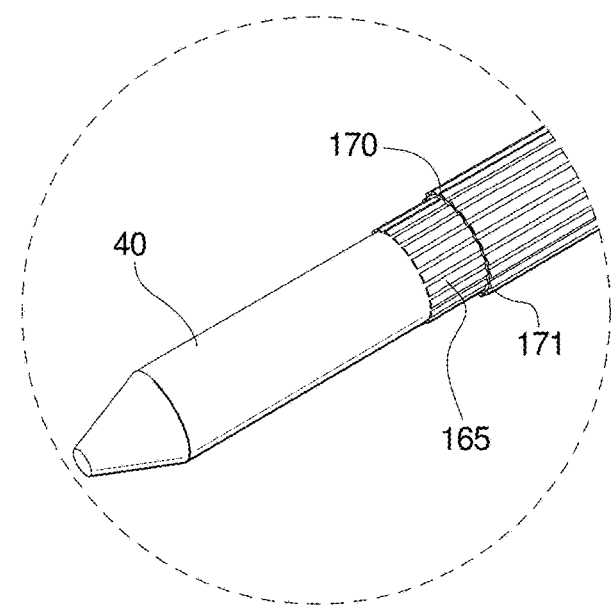
FIG. 12 is an enlarged view of the area circled and labelled 12 in FIG. 11.
Figure 13:
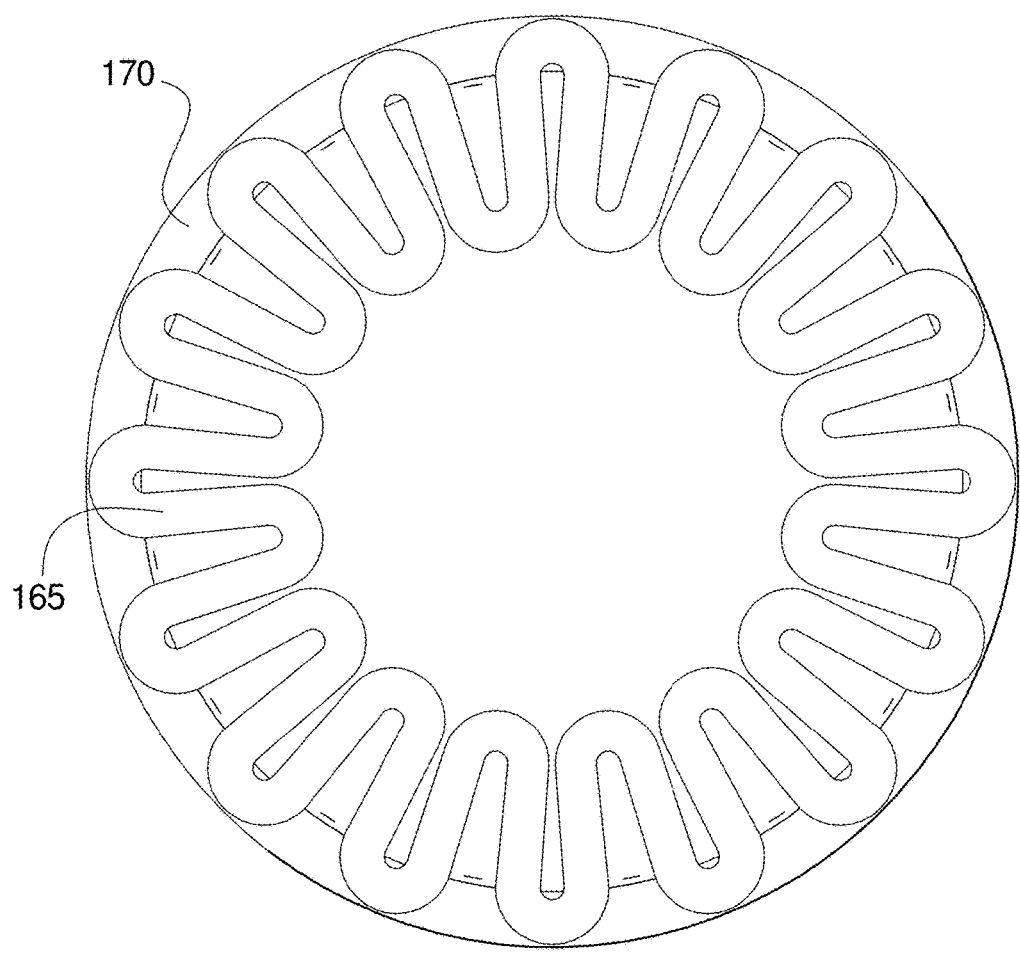
FIG. 13 is a cross sectional view of the embodiment shown in FIG. 11.

FIG. 11 shows an expandable introducer sheath 160 in accordance with another embodiment of this invention. FIG. 12 shows an enlarged view of the area circled and labelled 12 in FIG. 11. FIG. 13 shows a sectional view in the direction of the arrows D-D in FIG. 11. The expandable introducer sheath 160 comprises the hub 15 attached to a shaft 165 and the dilator 10 within the inner lumen of the shaft 165. The shaft 165 is corrugated as shown in FIG. 13 in an unexpanded configuration. The outer surface of the shaft 165 consists of a series of folded segments of shaft adjacent to each other around the circumference of the shaft. The radii of each folded section on the outer surface of shaft 165 are sufficiently large so as to be atraumatic when within a vessel. An O-ring 170 resides within a groove 171 on the outer surface of shaft 165 as shown in FIG. 12. The O-ring 170 serves to keep the shaft 165 in an unexpanded configuration. The O-ring 170 is recessed within the groove 171 on the outer surface of the shaft 165 so as to not cause an increase in profile (diameter) of the outer shaft and to ensure that the O-ring 170 may not catch or snag during advancing of the expandable introducer sheath 160 into a patient's vasculature. The shaft 165 may increase in internal diameter when devices are advanced through its lumen. The folds of the shaft 165 allow for a significant increase in the internal diameter during passage of devices through the sheath 160 to permit passage of the device along the sheath. The O-ring 170 serves to re-collapse or fold down the shaft 165 after it has been expanded. The shaft 165 may be formed from a polymer or non-polymer material by a process of extrusion or other processes. Alternately, the shaft 165 may be formed into the shape shown in FIG. 13. The O-ring 170 may be formed from an elastomeric or non-elastomeric material. The expandable introducer sheath 160 may comprise numerous O-rings evenly or unevenly spaced along the length of shaft 165 to ensure that there is sufficient elastic force to keep shaft 165 in a folded configuration. In alternate embodiments, elastomeric bands may be used to fulfil the same function as the O-ring 170.

Operation

The expandable introducer sheath 5 in FIG. 1 can be used during minimally invasive procedures for insertion into a patient's vessel in an unexpanded configuration. Prior to use the expandable introducer sheath 5 may be visually inspected for any defects. A syringe containing saline may be attached to the stopcock 25 and saline may be flushed through the tube 20, in through the hub 15, and into the annular space between the shafts 45 and the dilator 10 to remove any air that may reside in this cavity. The expandable introducer sheath 100 in FIG. 7 may be flushed in a similar manner but in this instance saline may be flushed through the tube 20, in through the hub 15, and into the annular space between the dilator 10 and the inner folded layer 105 shown in FIG. 8. The punch holes 120 may allow saline to flow from inside the inner folded layer 105 to outside the inner folded layer 105 to remove any potential air between the inner folded layer 105 and the outer elastomeric layer 50. The expandable introducer sheath 100 may be oriented with the dilator distal end 40 pointing upwards during flushing of saline through the stopcock 25 and verifying that saline exits from the distal end of the expandable introducer sheath 105. After flushing of saline through the stopcock 25, the tap of the stop cock 25 may be closed to ensure that no air may enter the tube 20 or the hub 15. A syringe containing saline may be attached to the Luer connector 35 of the dilator 10 and saline may be flushed through the inner lumen of the dilator to remove any potential air.

Prior to insertion of the expandable introducer sheath 5 into a patient's vessel, the vessel is accessed and a guide wire may be positioned within the vessel. The dilator distal end 40 of the expandable introducer 5 may be loaded onto the proximal end of the pre-positioned guide wire and the expandable introducer sheath 5 may be carefully advanced over the guide wire and into the patient's vessel. Once in position, the guide wire and the dilator 10 may be removed from the expandable introducer sheath 5. Other interventional devices may then be passed through the sealing valve 30 of the hub 15 of the expandable introducer sheath 5. The inner folded layer 55 of the expandable introducer sheath 5 may unfold to increase the internal diameter of the expandable introducer sheath 5 during passage of devices through the main lumen of the expandable introducer sheath. The outer elastomeric layer 50 may also expand in diameter when the inner folded layer 55 is unfolding. The inner folded layer 55 and the outer elastomeric layer 50 may reduce down in profile after passage of devices through the main lumen of the expandable introducer sheath 5.

According to a first aspect, an expandable introducer sheath, comprising: an inner folded shape-memory layer having an inside passage and an outer surface; and an elastomeric outer layer extending about the outer surface of the inner folded shape-memory layer; wherein the inner folded shape-memory layer has a first inside diameter in a folded condition and is expandable to a second inside diameter during passage of a device through the inside passage, the second inside diameter being greater than the first inside diameter; wherein the elastomeric outer layer is constructed to compress the inner folded shape-memory layer which has been expanded to the second inside diameter by passage of the device so that the inner folded shape-memory layer is compressed to a folded state that is less than the second inside diameter; wherein the expandable introducer sheath is constructed so as to be capable of atraumatic expansion within a patient's vessel during passage of a device through an inner lumen of said expandable introducer sheath and said expandable introducer sheath is constructed so as to be capable of a reduction in outer diameter after passage of a device thorough the inner lumen of the expandable introducer sheath.

According to a second aspect, an expandable introducer sheath as in the first aspect, wherein the inner folded shape-memory layer and the elastomeric outer layer define an annular space therebetween, wherein said inner folded shape-memory layer includes a wall, the wall defines holes that enables fluid to pass from an interior of the inner folded shape-memory layer into the annular space between the inner folded shape-memory layer and said outer elastomeric layer during purging of the expandable introducer sheath.

According to a third aspect, an expandable introducer sheath as in the first aspect, wherein said inner folded shape-memory layer includes a wall, the wall comprises thin portions of the wall along the fold lines to ease of folding and unfolding of the inner folded shape-memory layer.

According to a fourth aspect, an expandable introducer sheath as in the first aspect, wherein said inner folded shape-memory layer is recessed at a distal end in a region of folds of the inner folded shape-memory layer so as to gradually step up a profile of the distal end of the inner folded shape-memory layer.

According to a fifth aspect, an expandable introducer sheath as in the first aspect, wherein the inner folded shape-memory layer further comprises fold lines, the inner folded shape-memory layer defines perforations along the fold lines of said inner folded shape-memory layer that operate to ease folding and unfolding of said inner folded layer and also enables fluid to pass into an annular space between the inner folded shape-memory layer and the elastomeric outer layer during purging of the expandable introducer sheath.

According to a sixth aspect, an expandable shaft for use in interventional devices that comprises: an inner folded layer having an interior lumen and an outside surface; an elastomeric outer layer extending about the outside surface of the inner folded layer; wherein the inner folded layer and the elastomeric outer layer form the expandable shaft that is capable of atraumatic expansion and contraction.

According to a seventh aspect, an expandable shaft as in the sixth aspect, wherein the inner folded layer is heat set into a folded configuration that enables the inner folded layer to retain a folded shape and wherein the inner folded layer reverts to a folded configuration after expansion.

According to an eighth aspect, an expandable shaft for use in interventional devices as in the sixth aspect, wherein the inner folded layer includes a wall of the inner folded layer that is thinned along fold lines of the inner folded layer for ease of expansion and contraction of the expandable shaft.

According to a ninth aspect, an expandable shaft for use in interventional devices as in the sixth aspect, wherein the inner folded layer includes a wall that defines holes through the wall, the holes being configured to enable fluid to pass from inside the inner folded layer to outside the inner folded layer.

According to a tenth aspect, an expandable introducer sheath, comprising: a folded inner layer; an elastomeric outer layer extending about the folded inner layer; wherein the folded inner layer and the elastomeric outer layer form the expandable introducer sheath such that the expandable introducer sheath is capable of expansion and contraction within a patients vessel.

According to an eleventh aspect, an expandable introducer sheath as in the tenth aspect, wherein the elastomeric outer layer includes at least one elastomeric band on the inner folded layer, the at least one elastomeric band being recessed into a wall of the inner folded layer and the at least one elastomeric band being constructed to allow expansion of the folded inner layer during passage of a device through a lumen of the inner folded layer and the at least one elastomeric band being constructed to ensure the inner folded layer reverts back to a folded configuration after expansion; wherein the expandable introducer sheath is capable of atraumatic expansion and contraction.

According to a twelfth aspect, an expandable introducer sheath as in the tenth aspect, wherein the elastomeric outer layer includes at least one O-ring on the folded layer; wherein the expandable introducer sheath is constructed to be capable of atraumatic expansion within a patient's vessel during passage of a device through an inner lumen of the expandable introducer sheath and the expandable introducer sheath is constructed to be capable of a reduction in outer diameter after passage of a large profile device thorough a main lumen of the expandable introducer sheath.

According to a thirteenth aspect, an expandable shaft for use in interventional devices, that comprises: a folded layer in a form of a folded shaft; at least one ring along a length of the folded shaft to form the expandable shaft; wherein the expandable shaft is capable of atraumatic expansion and contraction.

According to a fourteenth aspect, an expandable shaft as in the thirteenth aspect, wherein the at least one ring is an O-ring.

According to a fifteenth aspect, an expandable shaft as in the thirteenth aspect, wherein the at least one ring is an elastomeric ring.

Thus, there is shown and described an expandable introducer sheath for use in interventional procedures. The expandable introducer sheath can be inserted into a treatment vessel in a first unexpanded configuration. The expandable introducer sheath can expand in diameter during insertion of a device through its main lumen and can then re-collapse down to its unexpanded diameter. The device comprises an inner heat-set folded layer and an outer elastomeric layer. The outer elastomeric layer provides a barrier between the inner folded layer and a vessel wall during unfolding of the inner folded layer to minimize the risk of vessel trauma.

Although other modifications and changes may be suggested by those skilled in the art, it is the intention of the inventors to embody within the patent warranted hereon all changes and modifications as reasonably and properly come within the scope of their contribution to the art.

We claim:

1. An expandable introducer sheath, comprising:
    a folded inner layer having an inner lumen and being formed of shape memory material, the folded inner layer being configured to expand from a contracted folded state to an expanded state upon passage of a device along the inner lumen, the shape memory material being configured to return the folded inner layer from the expanded state to the contracted folded state after the device has passed along the inner lumen of the folded inner layer; and
    an elastomeric outer layer extending about the folded inner layer, the elastomeric outer layer being configured to exert a compressive force on the folded inner layer at least when the folded inner layer is in the expanded state to aid the shape memory material of the folded inner layer in returning to the contracted folded state after expansion;
    wherein the folded inner layer and the elastomeric outer layer form the expandable introducer sheath such that the expandable introducer sheath is adapted for expansion and contraction when positioned within a patient's vessel, the folded inner layer being configured to refold to a compressed state after expansion and the elastomeric outer layer being configured to exert a compressive force on the folded inner layer during refolding to a compressed state.

2. The expandable introducer sheath as claimed in claim 1, wherein the elastomeric outer layer includes at least one elastomeric band on the folded inner layer,
    wherein the folded inner layer defines a recess extending about the folded inner layer transverse to an axis of the folded inner layer,
    wherein the at least one elastomeric band being disposed within the recess in the folded inner layer, the at least one elastomeric band being constructed to allow expansion of the folded inner layer to the expanded state during passage of the device through the inner lumen of the folded inner layer, the at least one elastomeric band being constructed to exert the compressive force on the folded inner layer in the expanded state to ensure that the shape memory material of the folded inner layer reverts back to a folded configuration after expansion; and
    wherein the expandable introducer sheath is configured for atraumatic expansion and contraction.

3. The expandable introducer sheath as claimed in claim 1, wherein the elastomeric outer layer includes at least one O-ring on the folded inner layer; and
    wherein the expandable introducer sheath is constructed for atraumatic expansion within the patient's vessel during passage of the device through the inner lumen of the folded inner layer and the expandable introducer sheath is constructed for a reduction in outer diameter after passage of a large profile device thorough a main lumen of the expandable introducer sheath by compression forces of the at least one O-ring acting on the shape memory material of the folded inner layer.

4. The expandable introducer sheath as claimed in claim 1, wherein the folded inner layer includes the inner lumen and an outside surface;
   wherein the elastomeric outer layer extending about the outside surface of the folded inner layer; and
   wherein the folded inner layer and the elastomeric outer layer form the expandable introducer shaft that is capable of atraumatic expansion and contraction.

5. The expandable shaft as in claim 4, wherein the folded inner layer is heat set into a folded configuration that enables the folded inner layer to retain a contracted folded state when not expanded by passage of a device along the inner lumen, and
   wherein the folded inner layer reverts to the folded configuration of the contracted folded state after expansion.

6. The expandable introducer sheath as in claim 4, wherein the folded inner layer includes a wall of the folded inner layer that is thinned along fold lines of the folded inner layer for ease of expansion of the folded inner layer from the contracted folded state to the expanded state and contraction of the folded inner layer from the expanded state to the contracted folded state.

7. The expandable introducer sheath as in claim 4, wherein the folded inner layer includes a wall that defines holes through the wall, the holes being configured to enable fluid to pass from inside the inner lumen of the folded inner layer to outside the folded inner layer when the folded inner layer returns to the contracted folded state from the expanded state.

8. The expandable introducer sheath as claimed in claim 1, wherein the elastic outer layer extends completely about the folded inner layer at at least one location along a length of the folded inner layer.

9. The expandable introducer sheath as claimed in claim 1, wherein the folded inner layer includes a wall, portions of the wall being disposed in overlying relation on one another to form overlying layers in a radial direction of the expandable introducer sheath when the folded inner layer is in the contracted folded state.

10. An expandable shaft for use in interventional devices, that comprises:
   a shape-memory folded layer in a form of a folded shaft having an interior lumen, the folded layer being formed of shape-memory material configured with a shape memory of a contracted folded state so that the folded layer reverts to the contracted folded state after being expanded to an expanded state; and
   at least one ring along a length of the folded shaft to form the expandable shaft, the ring being expandable when the folded layer expands to the expanded state, the ring exerting a contracting force on the folded layer to aid the folded layer in returning to the contracted folded state following expansion;
   wherein the expandable shaft is capable of atraumatic expansion and contraction, the shape-memory folded layer being configured to refold to a compressed state after expansion and the at least one ring being configured to exert a compressive force on the shape-memory folded layer during refolding to a compressed state.

11. The expandable shaft as claimed in claim 10, wherein the at least one ring is an O-ring.

12. The expandable shaft as claimed in claim 10, wherein the at least one ring is an elastomeric ring.

* * * * *